US006083701A

United States Patent [19]
Reeve

[11] Patent Number: 6,083,701
[45] Date of Patent: Jul. 4, 2000

[54] METHOD FOR DETERMINING TANDEM REPEAT SEQUENCE LENGTH

[75] Inventor: Michael Alan Reeve, Henley-on-Thames, United Kingdom

[73] Assignee: Amersham Pharmacia Biotech UK Limited, Buckinghamshire, United Kingdom

[21] Appl. No.: 09/117,492

[22] PCT Filed: Nov. 28, 1997

[86] PCT No.: PCT/GB97/03285

§ 371 Date: Dec. 7, 1998

§ 102(e) Date: Dec. 7, 1998

[87] PCT Pub. No.: WO98/23776

PCT Pub. Date: Jun. 4, 1998

[30] Foreign Application Priority Data

Nov. 28, 1997 [EP] European Pat. Off. .............. 96308668

[51] Int. Cl.[7] ............................... C12Q 1/68; C12P 19/34
[52] U.S. Cl. ............................................... 435/6; 435/91.2
[58] Field of Search ....................... 435/6, 91.2; 536/24.3

[56] References Cited

FOREIGN PATENT DOCUMENTS

| 0 721 016 A2 | 7/1996 | European Pat. Off. . |
| WO 91/15600 | 10/1991 | WIPO . |
| WO 95/21269 | 8/1995 | WIPO . |
| WO 96/31622 | 10/1996 | WIPO . |
| WO 96/36731 | 11/1996 | WIPO . |
| WO 97/27328 | 7/1997 | WIPO . |

OTHER PUBLICATIONS

Yaar, R. et al., "In situ detection of tandem DNA repeat length,"*Genetic Analysis: Biomolecular Engineering*, 13:113–118 (1996).

*Primary Examiner*—W. Gary Jones
*Assistant Examiner*—Jehanne Souaya
*Attorney, Agent, or Firm*—Marshall, O'Toole, Gerstein, Murray & Borun

[57] ABSTRACT

A method determining the number of repeats in a tandem repeat sequence of a nucleic acid target comprises providing an array of nucleic acid probes immobilized at spaced locations on a surface of a support. Each probe of the array has a tandem repeat sequence complementary to that in the target and containing a different number of repeats. When the target is hybridized with the array and forms a perfect match with the probe having the same number of repeats in the tandem repeat sequence, it is not removed by exonuclease treatment and can be detected on the array.

5 Claims, 1 Drawing Sheet

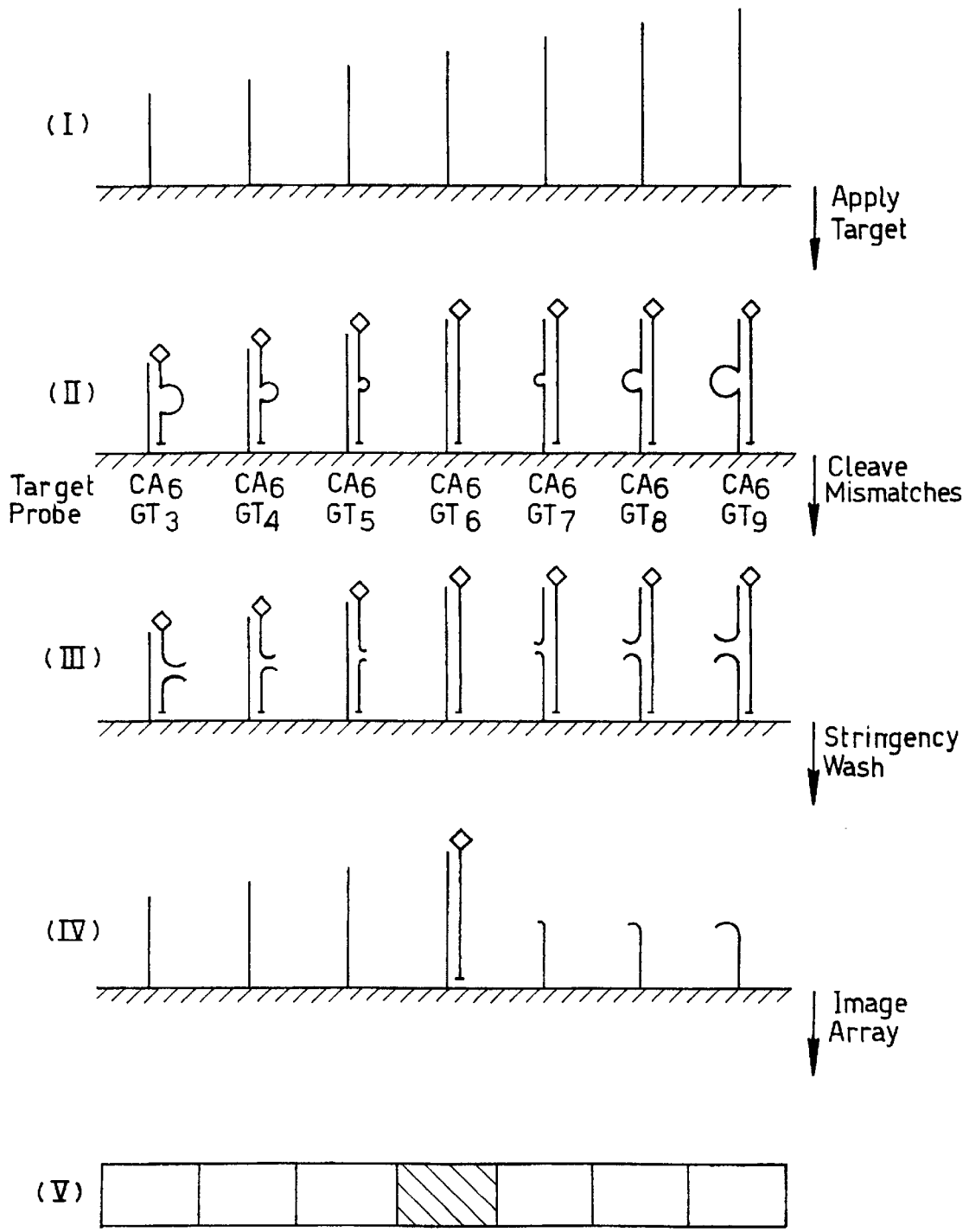

METHOD FOR DETERMINING TANDEM REPEAT SEQUENCE LENGTH

BACKGROUND OF THE INVENTION

Simple sequence repeats or microsatellites have found widespread usage in the linkage analysis of genetic traits. These sequences are tandem repeats of simple motifs that occur abundantly at random locations throughout the genomes of most eukaryotes. Microsatellites are ideal substrates for PCR due to the fact that they are generally flanked by unique sequence and the overall amplicon size is usually in the region of 100 bases. These sequences display polymorphic variation in the number of repeat units between the flanking sequences. The repeat length polymorphism is not only stable enough to facilitate genetic analysis but is also highly informative for the purpose of linkage analysis. Microsatellites thus serve as ideal markers for the construction of high resolution genetic maps and for the genomic localisation of regions of biological and medical interest.

Current methods for typing the number of repeats at such loci are time consuming and tedious. The number of repeats is determined by PCR product sizing in various electrophoretic separation systems. The PCR products generated upon amplification of genomic DNA may be labelled in a variety of ways. The currently preferred method employs the attachment of a fluorescent moiety to the PCR fragment in order to facilitate detection. A major limitation is the number of samples that can be analysed on a single gel. The current art—using multiple emission wavelength fluors—only allows up to about 10 PCR products to be analysed per gel lane.

In the current art, electrophoretic sizing of PCR products is complicated not only by mobility distortions introduced by the attached fluorescent moieties but also by the exact sequences chosen for the size markers (different sequence compositions for the same fragment length may result in small differences in mobility for some electrophoretic separation systems). Also, addition of non-template directed bases by the polymerase during PCR may lead to multiple fragments appearing in the electropherogram—complicating the subsequent analysis of repeat length considerably.

SUMMARY OF THE INVENTION

The present invention uses a hybridisation approach to obtaining information about microsatellite sequences. The system is immune to the electrophoretic mobility differences induced by such fluorescent moieties and is also insensitive to the addition of an extra base to the end of PCR fragments. Once set up, the system permits a rapid throughput and allows for the parallel analysis of a large number of different microsatellite repeat lengths.

In one aspect the invention provides a method of analysing a nucleic acid target comprising a tandem repeat sequence and two flanking sequences, which method comprises providing at least two nucleic acid probes in an array, each probe immobilised on a surface of a support and comprising a tandem repeat sequence and two flanking sequences complementary to the tandem repeat sequence and the two flanking sequences of the target, each probe immobilised at a spaced location on the surface of the support, the tandem repeat sequence length of one probe being different from that of another probe, labelling the target, applying the labelled target to the surface, washing the surface to remove labelled target that has not formed a perfectly matched hybrid with a probe, and using the label to observe a perfectly matched hybrid where the tandem repeat sequence of the target is the same length as the tandem repeat sequence of a probe.

BRIEF DESCRIPTION OF THE SEVERAL VIEWS OF THE DRAWINGS

FIG. 1 presents a schematic depiction of a method of practice of the invention.

DETAILED DESCRIPTION OF THE INVENTION

The nucleic acid target to be analysed comprises a tandem repeat sequence and two flanking sequences. The tandem repeat sequence contains a variable number (VNTR) of repeats of a simple motif. Generally analysis involves determining the number of repeats of that motif, or at least ascertaining whether the number of repeats in the target is the same as the number of repeats in a reference nucleic acid or probe. The nucleic acid target may conveniently be created or amplified by PCR. Suitable primers for amplifying many known tandem repeat sequences are well known and published in the literature.

The nucleic acid target is labelled. When the target is created or amplified by PCR, the label may conveniently be introduced by use of a labelled primer or labelled nucleotide. Labelling may alternatively be performed by enzymatic means without PCR, using dNTPs or analogues thereof. Labelling may also be performed by non-enzymatic means such as chemical coupling. When PCR is used, the unlabelled strand is preferably (though not necessarily) destroyed by enzymatic means well known to the skilled reader; for example a nuclease may be used that works from the 5' end but is inhibited by the presence there of a fluorescent or other label group.

The label may be chosen from those well known in the field, including radioactive isotopes, enzymatic labels that generate chemiluminescence or colour, label suitable for analysis by mass spectrometry or refractive index effects (e.g. surface plasmon resonance), and particularly fluorescent groups.

The label may be attached at any position on the nucleic acid target, generally at the 5'- or 3'-end.

It may be convenient to perform two or more PCR reactions simultaneously, e.g. by adding two or more pairs of PCR primers together to genomic DNA.

The method of the invention involves the use of at least two nucleic acid probes immobilised on a support, each comprising a tandem repeat sequence and two flanking sequences complementary to the tandem repeat sequence and the two flanking sequences of the target. Each nucleic acid probe is likely to comprise a chain of at least ten monomer units, but beyond that its length is immaterial. Each probe may be DNA, RNA, PNA, other nucleic acid mimetics or mixtures thereof. Each probe may be single stranded or partially double stranded, provided that a single strand is available for hybridisation with the target. Each probe may also contain one or more partially or wholly degenerate bases that pair with two or all four DNA bases, such as 5-nitroindole, 3-nitropyrrole or inosine. Each probe may likewise contain one or more bases such as 2-aminopurine or 5-methylcytosine that may improve its hybridisation properties.

Each nucleic acid probe has a tandem repeat sequence that is complementary to the tandem repeat sequence of the target. By this it is to be understood that the repeated motif in the probe is complementary to the repeated motif of the target. But the number of repeats in the probe is not necessarily the same as the number of repeats in the target. The number of repeats in each probe will generally, but not necessarily, be known.

At least two nucleic acid probes are provided in an array, each probe immobilised at a spaced location on a surface of a support, the tandem repeat sequence length of one probe being different from that of another probe. Preferably the array comprises different probes having all possible lengths of the tandem repeat sequence. Thus for example, if a particular tandem repeat sequence is known to occur from three to nine times in the genome, a particular target containing the tandem repeat sequence can by analysed by means of an array of seven probes, each having a different number from three to nine of tandem repeats of the motif in question.

Each nucleic acid probe of the array is immobilised at a spaced location on a surface of a support. Arrays may be provided on glass, plastic, silicon, supported membrane and supported gel substrates. A given support may carry sets of probes for various different tandem repeat sequences. Thus it is thought that $10^4$–$10^5$ tandem repeat sequences may be present scattered through the human genome. Arrays of tens or hundreds of thousands of oligonucleotides can be made using present day technology. An array for use in the method of this invention might comprise a set of probes directed against each known tandem repeat sequence in the human genome.

The probes of the array may be attached to the surface of the support through their 3'-ends or their 5'-ends. For in situ synthesis, it may be more convenient to provide probes immobilised at their 3'-ends. But for the purposes of this invention, either arrangement is suitable. It is an advantage of the invention that the probes do not need to be labelled.

The method of the invention involves applying the labelled target, in solution to the array of probes under hybridisation conditions. The target hybridises to each probe; forming a perfect match (a "match") if the number of repeats in the tandem repeat sequence of the probe is the same as in the target; or an imperfect match (a "mismatch") if the two numbers are different. In order to observe whether there is a match or a mismatch, it is necessary to discriminate between perfect and imperfect hybridisations. This is well within the competence of a skilled reader, and possible techniques are discussed below.

By way of example, a nucleic acid target is a length of genomic double stranded DNA containing a tandem repeat sequence which in the forward strand is $(CA)_6$ and in the reverse strand is $(GT)_6$. This target is amplified by PCR, using as primers the flanking sequences surrounding the tandem repeat sequence, one primer being labelled with a fluorescent label. The result is a single stranded fluorescently labelled nucleic acid target comprising the tandem repeat sequence $(CA)_6$ and the two flanking sequences.

Reference is directed to the accompanying drawing, which is a flow diagram showing operation of one example of a method according to the invention. An array of nucleic acid probes (I) contains seven probes each comprising a tandem repeat sequence $(GT)_n$ where n is from 3 to 9 and two flanking sequences complementary to the target. When the labelled target is applied to the array under hybridisation conditions, it forms a match with the $(GT)_6$ probe and mismatches with the other six probes (II). In order to discriminate between matches and mismatches, the mismatches are cleaved under conditions such that only the perfect match is unaffected (III). Then the array is subjected to a stringency wash to remove the labelled target except at the location of the perfect match (IV). Finally the array is visualised and the location of the match (at the $(GT)_6$ probe) is observed (V), as an indication that the number of repeats in the tandem repeat sequence of the target was six.

In the drawing, the nucleic acid target is shown carrying a label (shown as an open diamond) at the end remote from the surface of the support to which oligonucleotide probes are tethered. But the method of the invention would work equally well if the nucleic acid target were labelled at the other end.

Numerous methods are available to discriminate between the perfectly matched hybrid and repeat number mismatched hybrids.

Enzymatic means may be used in order to cleave the repeat number mismatched species. Many such methods will be obvious to those skilled in the art. Nucleases that are single strand specific such as SI nuclease, mung bean nuclease, T4 endonucleaseVII, deoxyinosine 3'-endonuclease and RNase A are just some of many possible examples.

Nucleases may be used in order to effect the complete destruction of the strand that is partially single stranded where a repeat number mismatch occurs. The array is washed at raised stringency in order to discriminate between the longer perfect duplex and the nicked or gapped products arising from cleavage of repeat number mismatched duplexes.

An alternative to raised stringency washing at increasing temperature, increased denaturants or decreased salt as above that will be obvious to those skilled in the art is the application of altered array element electrostatic potential relative to the rest of the array or bulk solution. For example, biasing a series of array element with negative potential relative to the rest of the array will force the repeat number mismatched hybrids off the array before the perfectly matched duplex as the degree of negative bias is increased.

In addition to enzymatic means as described above, chemical means may be used in order to selectively cleave or degrade the repeat number mismatched species. Many such methods will be obvious to those skilled in the art. chemical treatments that are single strand specific such as osmium tetroxide and hydroxylamine are just some of many possible examples.

Depending on the nature of the label chosen, the labelled target may be detected by means of fluorescence (emission, lifetime or polarisation), absorption, colour, chemiluminescence, enzymatic activity, radioactive emission, mass spectroscopy or refractive index effects (e.g. surface plasmon resonance). A plurality of nucleic acid targets can be simultaneously assayed for the same tandem repeat sequence, by labelling each target separately with a different label, e.g. a fluor having a characteristic emission wavelength distribution, and then applying the mixed targets to a nucleic acid probe array as described.

The method of the invention has an advantage over other similar techniques. A situation is envisaged where two genetic loci (A and B) are being investigated. The alleles at A and B may contain various numbers of repeat sequences. In a simple experiment, it would be possible to perform one PCR reaction with locus A flanking primers (Af and Ar for the forward and reverse direction), and a separate PCR reaction for the locus B flanking primers (Bf and Br). Then the AfAr PCR products and the BfBr PCR products are pooled and then assayed for repeat unit number as described herein. But the need to perform a separate PCR reaction for each locus makes the method expensive.

An alternative approach is to carry out both PCR reactions simultaneously by adding both pairs of PCR primers to the same DNA. When this is done, there may be a risk of spurious "primer cross-talk" PCR products (e.g. AfBr and BfAr) being formed. However the probes in the array of the present invention are only complementary to the form Af-repeat-Ar or Bf-repeat-Br. Cross-talk products cannot therefore form perfect hybrids with probes of the array and will consequently be subjected to enzymatic digestion and differential washing in the same manner as the hybrids with different numbers of repeat units on each strand.

With existing methods, problems are encountered with cross-talk products at even modest levels of PCR multiplexing. It is an advantage of the method of this invention that the assay technique permits a greater degree of PCR multiplexing, in order to create a mixture of nucleic acid targets for assay, then has conventionally been possible. In the practical operation of the method, this advantage is expected to be important.

The method of the invention has potential applicability in the following areas—linkage analysis, genetic mapping, positional cloning, identity testing, paternity testing, pedigree verification, and the analysis of simple repeat based diseases such as Huntingdon's disease.

In another aspect, the invention provides a kit for analysing nucleic acid targets, comprising the array as described and reagents comprising primers, nucleotides and polymerase for making nucleic acid targets by PCR.

What is claimed is:

1. A method of analysing a nucleic acid target comprising a tandem repeat sequence and two flanking sequences, which method comprises providing at least two unlabelled nucleic acid probes in an array, each probe immobilised on a surface of a support and comprising a tandem repeat sequence and two flanking sequences complementary to the tandem repeat sequence and the two flanking sequences of the target, each probe immobilised at a spaced location on the surface of the support, the tandem repeat sequence length of one probe being different from that of another probe, labelling the target, applying the labelled target to the surface, subjecting the surface to a high stringency wash to remove labelled target that has not formed a perfectly matched hybrid with a probe, and using the label to observe a perfectly matched hybrid on said array where the tandem repeat sequence of the target is the same length as the tandem repeat sequence of a probe.

2. A method as claimed in claim 1, wherein the nucleic acid target has been created or amplified by PCR.

3. A method as claimed in claim 1, wherein the label has been introduced by the use of a labelled primer or labelled nucleotide in the PCR.

4. A method as claimed in claim 1, wherein the array comprises different probes having all possible lengths of the tandem repeat sequence.

5. A method as claimed in claim 1, wherein removal of the labeled target that has not formed a perfectly matched hybrid with a probe is effected by the use of a nuclease that is single strand specific followed by a high stringency wash.

* * * * *